United States Patent [19]
Ghorashi et al.

[11] Patent Number: 5,178,007
[45] Date of Patent: Jan. 12, 1993

[54] AUTOMATIC FIBER BUNDLE TESTING APPARATUS

[75] Inventors: Hossein M. Ghorashi; Martin M. Inman; Ian F. Oxley; C. Roger Riley, Jr.; Glenn E. Irick, Sr.; James D. Needham, all of Knoxville, Tenn.

[73] Assignee: Zellweger Uster, Inc., Knoxville, Tenn.

[21] Appl. No.: 761,320

[22] Filed: Sep. 17, 1991

[51] Int. Cl.⁵ .................. G01N 33/36; G01N 1/04
[52] U.S. Cl. ........................ 73/159; 73/160
[58] Field of Search .................. 73/159, 160

[56] References Cited

U.S. PATENT DOCUMENTS

| | | | |
|---|---|---|---|
| 3,444,728 | 5/1969 | Burns | 73/159 |
| 4,733,829 | 3/1988 | Mima | 73/160 |
| 4,862,741 | 9/1989 | Heusser | 73/159 |

FOREIGN PATENT DOCUMENTS

| | | | |
|---|---|---|---|
| 0640112 | 1/1979 | U.S.S.R. | 73/159 |
| 1193560 | 11/1985 | U.S.S.R. | 73/159 |

OTHER PUBLICATIONS

Spinlab HVI 900 System, Zellweger Uster, pp. 1, 4, 5, 7 (no date).

Primary Examiner—William A. Cuchlinski, Jr.
Assistant Examiner—Diego F. F. Gutierrez
Attorney, Agent, or Firm—Luedeka, Hodges, Neely & Graham

[57] ABSTRACT

An apparatus (20) for testing a specimen sample of fibers includes a frame (22), rotatable drums (60) situated at a first station upon the frame for holding a quantity (86) of fibers, a brush (152) situated at a second station along the frame for brushing the fiber specimen and testing equipment (28) situated at a third station upon the frame for performing a series upon the fiber specimen. A comb (34 or 35) is utilized for gathering the fiber specimen from the quantity of fibers held by the drums, and carriages (122 and 136) are movably mounted upon the frame for transporting the comb between the first, second and third stations of the apparatus. When positioned at the first station, the comb gathers a fiber specimen, and the specimen is carded. When the comb is positioned at the second station, the gathered specimen is brushed by the brush, and when the comb is thereafter moved to the third station, the brushed specimen is tested by the testing equipment. The apparatus also includes a controller (38) for controlling various components of the apparatus so that the operation of the apparatus is carried out automatically.

20 Claims, 9 Drawing Sheets

AUTOMATIC FIBER BUNDLE TESTING APPARATUS

BACKGROUND OF THE INVENTION

This invention relates generally to the obtaining particularly, is concerned with apparatus with which such test data is obtained.

Typical steps involved in the obtaining of test data from a fiber bundle, such as a cotton sample, include the gathering of a specimen sample from a larger amount of fibers, preparing the specimen for testing and then performing a number of tests upon the prepared specimen. The preparing of a specimen sample for testing may involve carding and brushing of the specimen fibers, and the tests performed upon the specimen may measure such characteristics as the strength and density of the specimen fibers. The measured characteristics may ultimately be used in the regulation of the marketing and procurement of raw fiber, the selection of fiber bales for use, or in the control of inventory.

There exists a known system which is capable of automatically brushing and then presenting the brushed specimen to test equipment where tests are automatically carried out upon the specimen. Heretofore, however, the steps of gathering of a specimen sample from a larger amount of fibers and the carding of the gathered specimen have been performed independently of the aforementioned system so that transference of a carded specimen to the aforementioned system must be conducted manually. It would be desirable to provide a system wherein the steps of gathering and carding a specimen sample are carried out automatically and then the carded specimen is automatically brushed and tested.

Accordingly, it is an object of the present invention to provide a new and improved apparatus which automatically gathers a specimen sample of fibers from a larger amount of fibers, prepares the specimen sample for testing and then performs the testing operation upon the specimen.

Another object of the present invention is to provide such an apparatus which is easy to use, performs its operations quickly and is effective in operation.

SUMMARY OF THE INVENTION

This invention resides in an apparatus for testing a specimen sample of fibers.

The apparatus includes sample holding means for holding a quantity of fibers from which a specimen of fibers is to be gathered for testing and testing means for performing at least one test upon the specimen of fibers. The testing means is situated for performing a test upon the specimen of fibers when the sample is positioned in registry with the testing means. The apparatus also includes sampling means for gathering a fiber specimen from the quantity of fibers held by the sample holding means and for holding the specimen during testing operations performed upon the specimen. A movable carriage is also included for supporting the sampling means, and carriage moving means are associated with the carriage for moving the carriage so that the sampling means is positionable adjacent the sample holding means for gathering a specimen of fibers from the quantity of fibers held by the holding means and is positionable adjacent the testing means so that the fiber specimen is positioned in registry with the testing means for performing a test upon the fiber specimen.

DETAILED DESCRIPTION OF THE ILLUSTRATED EMBODIMENT

Figure 1:
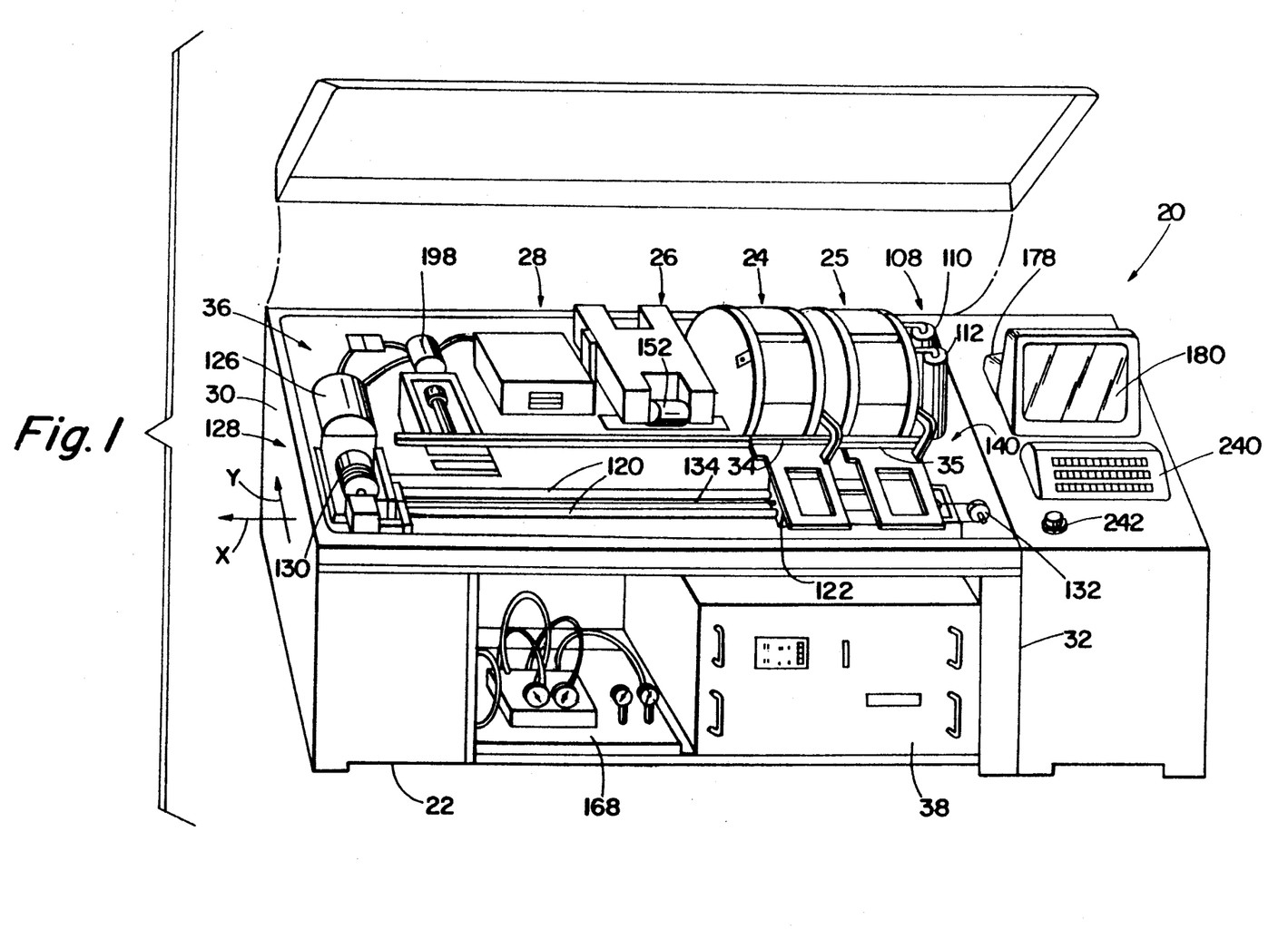
FIG. 1 is a perspective view of a fiber testing apparatus within which features of the present invention are incorporated.
Figure 2:
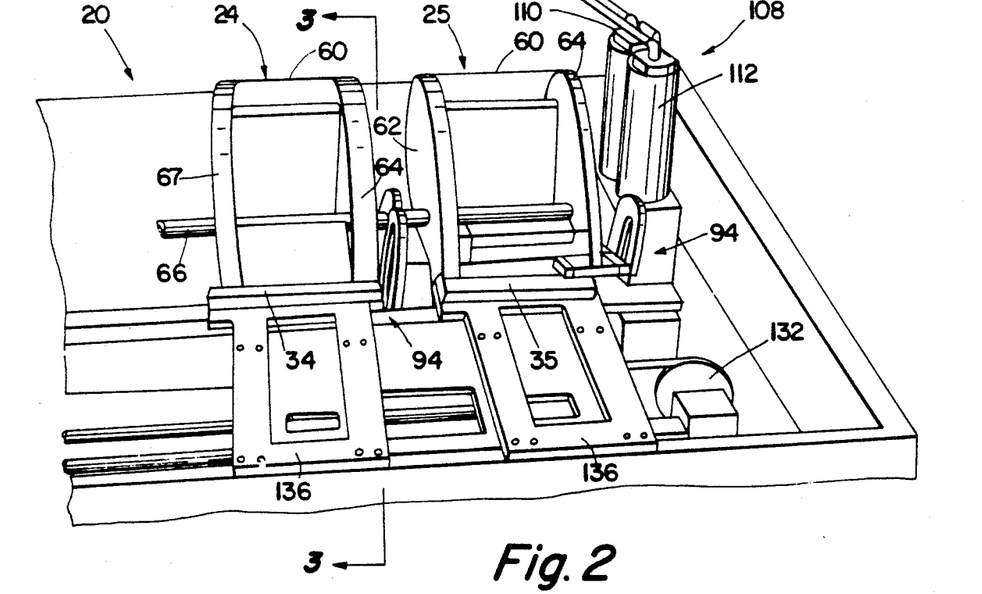
FIG. 2 is a fragmentary perspective view of the FIG. 1 apparatus as seen generally from the front of the apparatus.

Turning now to the drawings in greater detail, there is illustrated in FIG. 1 an apparatus, generally indicated 20, for performing tests upon specimen fiber bundles. The apparatus 20 includes a frame 22, a pair of sample holding means 24, 25 for holding a quantity of fibers from which fiber specimens are taken, brushing means 26 for brushing the fiber specimens and testing means 28 for performing tests upon the fiber specimens. The frame 22 is elongated in shape with two opposite ends 30, 32, and each of the aforementioned holding means 24, 25, brushing means 26, and testing means 28 are supported by the frame 22 at different stations therealong. As will be described in greater detail herein, a fiber specimen sample is gathered at a collection station adjacent the holding means 24 or 25, then transported to a brushing station adjacent the brushing means 26 where the specimen is brushed and then to a testing station adjacent the testing means 28 where the specimen is tested. The apparatus 20 includes sampling means in the form of a pair of combs 34, 35 for collecting fiber specimens from the holding means 24 and 25 and for retaining the specimens during the subsequent brushing and testing operations. The apparatus 20 also includes moving means 36 for transporting the combs 34, 35 and the specimens held thereby between the collection station and the brushing and testing stations. Still further, the apparatus 20 includes a computer controller 38 for controlling the operation of various ones of the aforementioned apparatus components.

Figure 4:
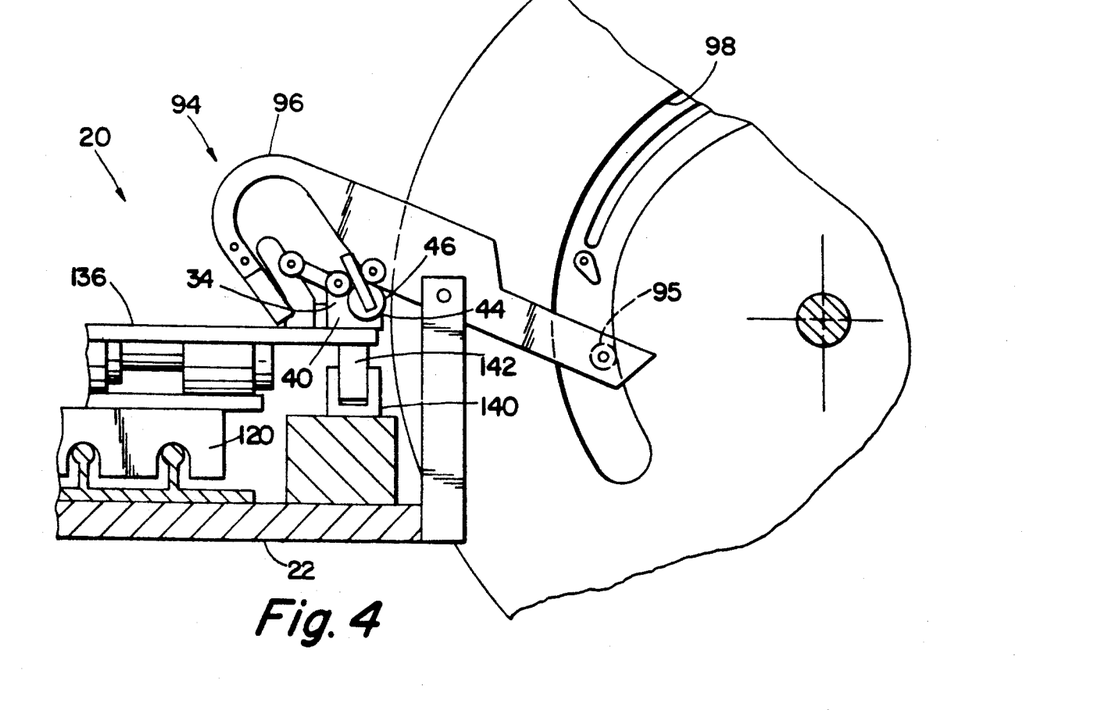
FIG. 4 is a view similar to that of FIG. 3 illustrating the apparatus comb in its closed position.
Figure 5:
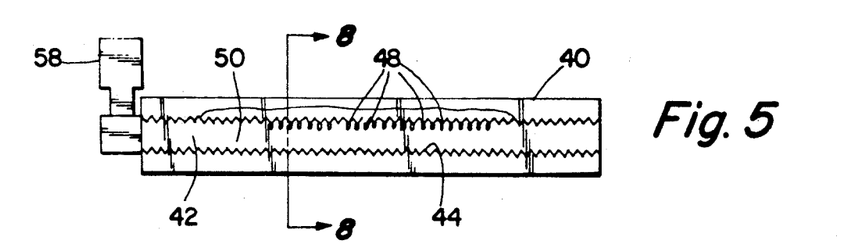
FIG. 5 is an elevational view of the comb of FIG. 3 as viewed generally along the line 5—5 of FIG. 3.
Figure 6:
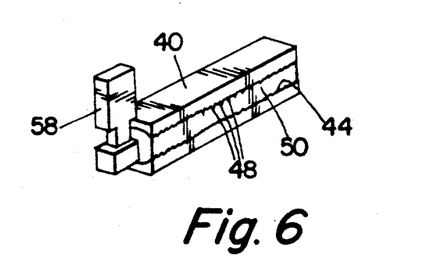
FIG. 6 is a fragmentary perspective view of the FIG. 5 comb shown positioned in its opened position.

As exemplified by the comb 34 of FIGS. 2-9, each comb 34 or 35 includes an elongated brass body 40 and a rotatable steel clamp 42 positioned within the body 40. The body 40 has an internally-threaded interior having a side opening 44 opening out of one side, or the right side as viewed in FIGS. 3 and 4, of the body 40, and the clamp 42 has a generally cylindrical exterior having a threaded peripheral section 54 having threads which mate with those of the body 40 to retainably secure the clamp 42 within the body 40. The exterior of the clamp 42 further includes a flat peripheral region having a smooth surface 50 which is positioned in registry with the side opening 44, as best shown in FIG. 6, when the clamp 42 is positioned in one rotational position with respect to the comb body 40.

Figure 3:
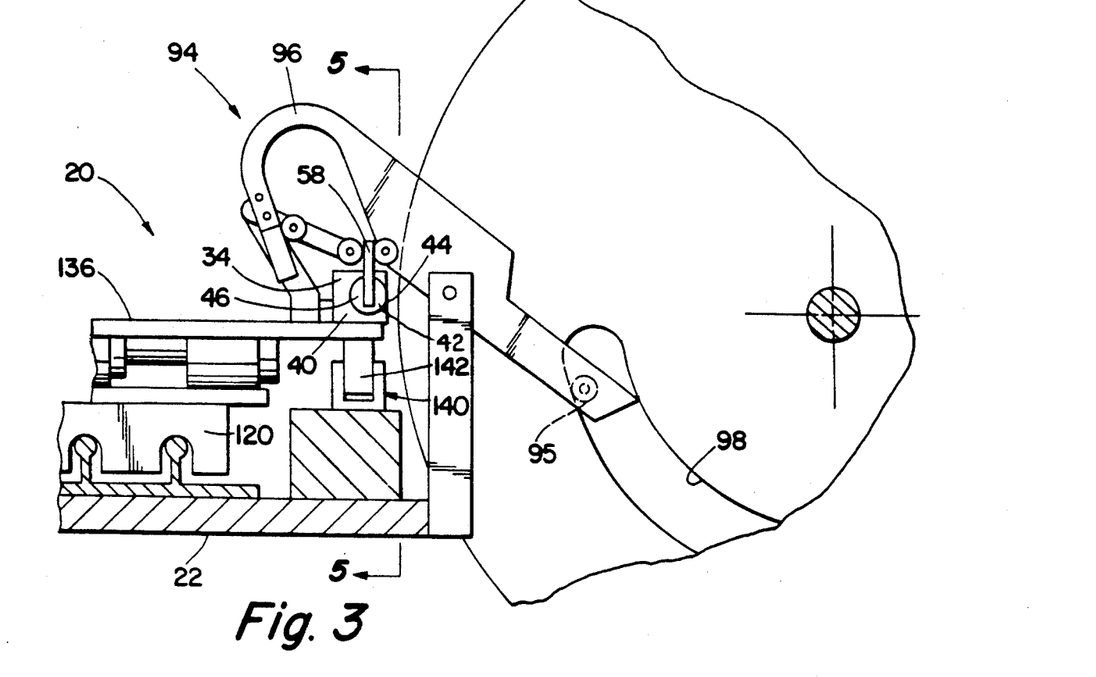
FIG. 3 is a cross-sectional view of a fragment of the FIG. 1 apparatus taken about along line 3—3 of FIG. 2 and illustrating a comb of the apparatus in its opened position.
Figure 7:
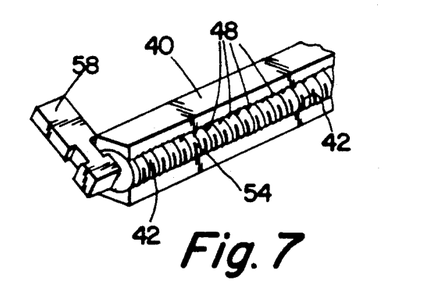
FIG. 7 is a fragmentary perspective view of the FIG. 5 comb shown positioned in its closed position.
Figure 8:
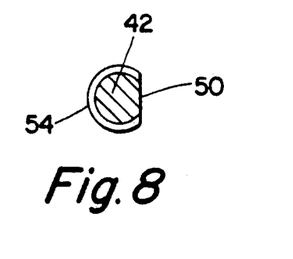
FIG. 8 is a cross-sectional view of the clamp of the FIG. 5 comb taken along about line 8—8 of FIG. 5.
Figure 9:
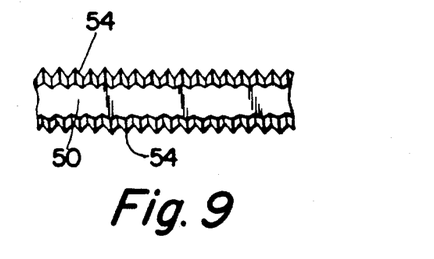
FIG. 9 is an elevational view of a fragment of the FIG. 8 comb clamp as seen generally from the right in FIG. 8.

Each comb 34 or 35 further includes a plurality of needles 48 secured, as by soldering, to the comb body 40 adjacent the side opening 44 so as to be directed downwardly thereacross as shown in FIGS. 5, 6 and 7. When each comb 34 or 35 is positioned adjacent a corresponding one of the holding means 24 or 25 and its clamp 42 is positioned with its flat surface 50 in registry with the side opening 44 as illustrated in FIG. 3, the needles 48 are in a condition to gather fibers when a quantity of fibers held along the periphery of the holding means 24 or 25 is moved upwardly past the comb 34 or 35 in a manner described herein. When the comb clamp 42 is subsequently rotated in a counter-clockwise direction as viewed in FIG. 4 to the position illustrated in FIG. 7, the threads of the clamp 42 are accepted by the gaps provided between the needles 48 to secure the gathered fibers to the comb 34 or 35. As will be apparent herein, the clamp 42 is in an opened position when positioned so that its flat surface 50 is in registry with the comb body opening 44 as shown in FIGS. 3, 5 and 6 and is in a closed position when rotated to its position shown in FIGS. 4 and 7. To facilitate movement of the clamp 42 between its opened position and its closed position, a lever 58 is fixedly secured to one end of the clamp 42 as best shown in FIGS. 5-7.

Figure 10:
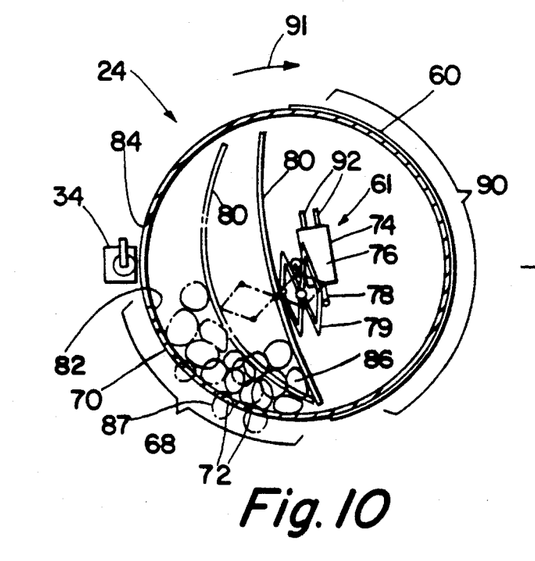
FIG. 10 is a schematic cross-sectional view of a drum of the FIG. 1 apparatus illustrated in a first rotational position.
Figure 11:
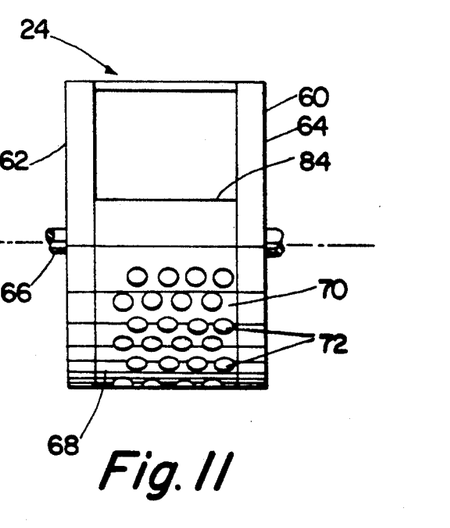
FIG. 11 is a schematic elevational view of the FIG. 10 drum as viewed from the left in FIG. 10.

With reference to FIGS. 10-13, each of the sample holding means 24 or 25 includes a drum 60 having a pair of circular side plates 62, 64 and arcuate surface portions extending between the side plates 62, 64. Each drum 60 is supported within the frame 22 for rotation about a horizontal axis which extends through the center of the side plates 62, 64. In this connection, both drums 60 are fixed about an axle 66 which is journaled within the frame 22 for rotation of the drums 60 as the axle 66 is rotated. One arcuate foraminous surface portion, indicated 68, of each drum 60 is provided by an arcuate plate 70 having a plurality of holes 72 disposed across its surface as best shown in FIG. 11.

Suitably mounted within each drum 60 is a presser 61 including a double-acting air cylinder 74 having a cylinder 76 which is mounted in a stationary condition within the drum 60 for rotation therewith and a movable ram 78 positioned within the cylinder 76 for longitudinal movement relative to and along the length of the cylinder 76. A thin hand plate 80 which is constructed, for example, of plastic is arranged within each drum 60 adjacent the arcuate plate 70 and is connected to the ram 78 by a suitable linkage arrangement 79 so that movement of the ram 78 between extended and retracted positions within the cylinder 76 moves the hand plate 80 between a retracted position as illustrated in solid lines in FIG. 10 and an extended position as illustrated in phantom in FIG. 10. As the hand plate 80 is moved from its retracted to its extended position, the hand plate 80 moves closer to the arcuate plate 70 and flex from the FIG. 10 solid line condition to the FIG. 10 phantom-line condition. With reference to FIGS. 10-13 and 22, the air cylinder 74 is connected to an air pressure source 88 by means of hoses 92 routed through one of the side plates 62, 64, and the actuation of the cylinders 74 is controlled by way of suitable valves 170 interposed within the hoses 92. The hand plate 80 spans the width of the drum interior and provides, with the arcuate plate 70, a hopper section 82 (FIG. 10) within which a quantity, indicated 86, of fibers are positionable. Access to the hopper section 82 may be had through an access opening 84 provided between the side plate 62, 64 adjacent the arcuate plate 70.

Figure 14:
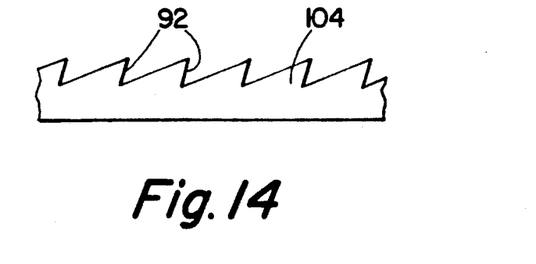
FIG. 14 is an elevational view of a fragment of the card wire used with the drum of FIGS. 10-13.

Each drum 60 also includes an arcuate portion 90 extending between its side plates 62, 64 which supports means 102 for carding the fiber specimen gathered by the comb 34 or 35 in a manner described herein. In the depicted apparatus 20, the carding means 102 is provided by an arrangement of card wire 104 (FIGS. 13 and 14) covering a substantial amount of the surface portion 90. As shown in FIG. 14, the card wire 104 has a saw-toothed-shaped profile with inclined surface regions terminating at flat surfaces 92 and is wrapped about the arcuate portion 90 so that the flat surfaces 92 face the direction corresponding with the direction in which the drum 60 is rotated at the beginning of an operation cycle. In the depicted apparatus 20, each drum 60 is rotated in the clockwise direction indicated by the arrow 91 in FIG. 10 at the beginning of an operation cycle and rotated in the opposite counter-clockwise direction indicated by the arrow 93 in FIG. 12 near the completion of an operation cycle. As will be apparent herein, the card wire 104 cards the fiber specimen held by the comb 34 or 35 when the drums 60 are rotated in the clockwise direction and knocks fibers loose from the comb 34 or 35 when the drums are rotated in the counter-clockwise direction. Card wire of the type suitable for use in the apparatus 20 is available in rolls from J. D. Hollingsworth on Wheels of Greenville, S.C.

Figure 12:
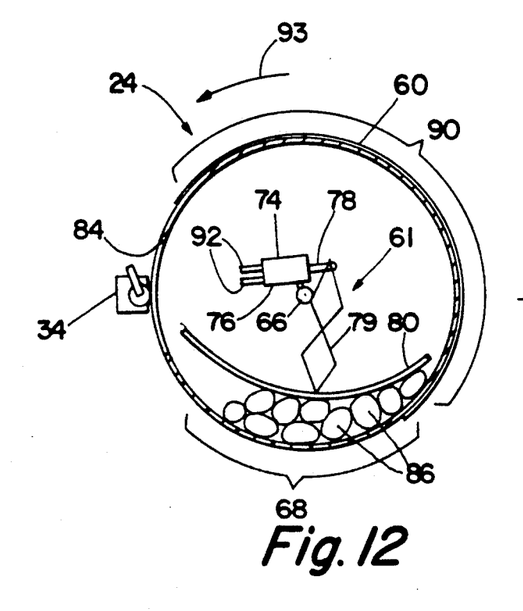
FIG. 12 is a view similar to that of FIG. 10 illustrating the drum of the FIG. 1 apparatus when positioned in a second rotational position.
Figure 13:
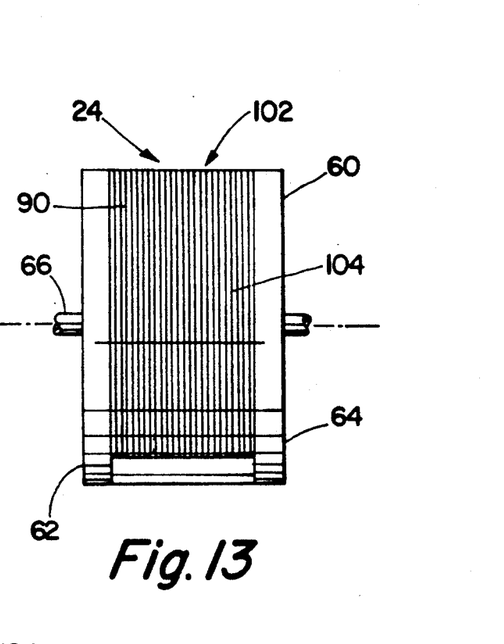
FIG. 13 is a schematic elevational view of the FIG. 12 drum as viewed from the right in FIG. 12.
Figure 15:
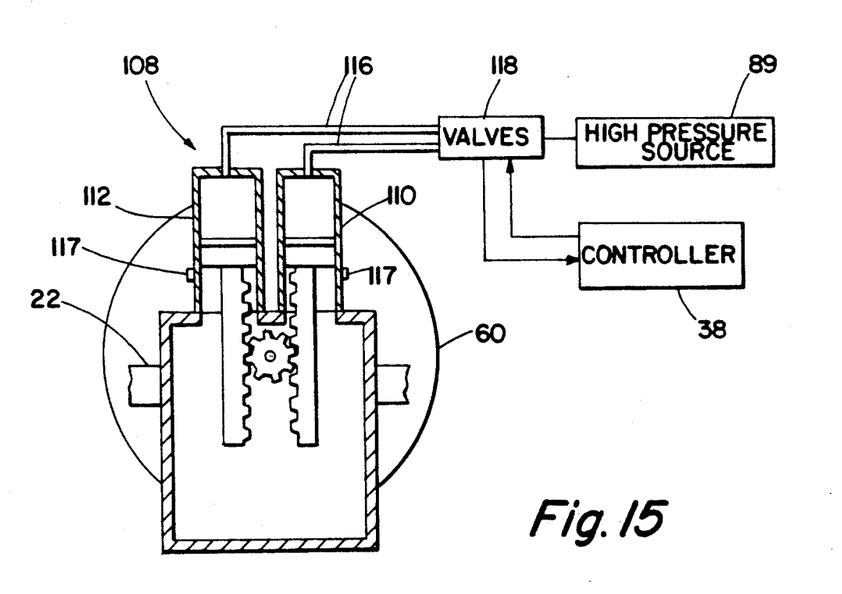
FIG. 15 is a schematic cross-sectional view illustrating the means by which the drums of the FIG. 1 apparatus are rotated.

Each drum 60 is rotatable between a first rotational, or start, position as illustrated in FIG. 10 at which the hopper section 82 is loaded with a quantity 86 of fiber and a second rotational, or end, position as illustrated in FIG. 12. In order to rotate the drums 60 between the FIG. 10 and FIG. 12 positions and with reference to FIGS. 1 and 15, a fluid-actuated cylinder arrangement 108 is mounted upon the frame 22 including a pair of single-acting cylinders 110, 112. Each cylinder 110 or 112 includes an internal piston which is suitably geared to the drum axle 66 so that actuation of one cylinder 110 forces its piston downwardly, as viewed in FIG. 15, to rotate the axle 66 in a clockwise direction as viewed in FIG. 10 and so that actuation of the other cylinder 112 forces its piston downwardly to rotate the axle 66 in a counter-clockwise direction as viewed in FIG. 10. Each cylinder 110 or 112 is vented through vents 117 at the end of its piston stroke, and the clockwise and counter-clockwise limits of rotation of the drums 60 are defined by the limits of movement of the pistons of the cylinders 110, 112. Each cylinder 110, 112 is connected to a source 89 of pressurized fluid through hoses 116, and the actuation of the cylinders 110, 112 is controlled by the controller 38 by way of valves 118 suitably connected to the hoses 116.

At the outset of an operation cycle with the apparatus 20, each comb 34 or 35 is supported by the moving means 36 at a sample-collection station adjacent a corresponding one of the drums 60 as illustrated in FIG. 1 and its clamp 42 is opened, and each drum 60 is positioned in its FIG. 10 start position. Within each drum 60, the hand plate 80 is positioned in a retracted position as illustrated in solid lines in FIG. 10. The hopper section 82 is then loaded with a quantity 86 of fibers which are manually inserted through the access opening 84. The cylinder assembly 74 is thereafter actuated so that the hand plate 80 is moved toward its extended position as illustrated in phantom in FIG. 10 so the fiber quantity 86 is urged by the hand plate 80 against the inside surface of the arcuate plate 70. As the fiber quantity 86 is pressed against the inside surface of the arcuate plate 70, a portion, indicated 87 in FIG. 10, of the sample quantity 86 protrudes through the holes 72 provided in the plate 70.

Each drum 60 is subsequently rotated by the cylinder assembly 108 in a clockwise direction as viewed in FIG. 10 so that the arcuate plate 70 sweeps past the comb 34 or 35 and so that a portion of the fiber quantity 86 which protrudes through the holes 72 in the arcuate plate 70 are caught by the needles 48 (FIG. 5) of the comb. Once the arcuate plate 70 has moved past the comb 34 or 35, the comb clamp 42 is moved to its closed position, best shown in FIG. 7, to thereby trap fibers which have been caught in the needles 48. The drum 60 thereafter continues its clockwise rotation so that the arcuate portion 90 moves past the comb 34 or 35 in an operation which cards the fiber specimen held by the comb 34 or 35 with the card wire 104.

Figure 16:
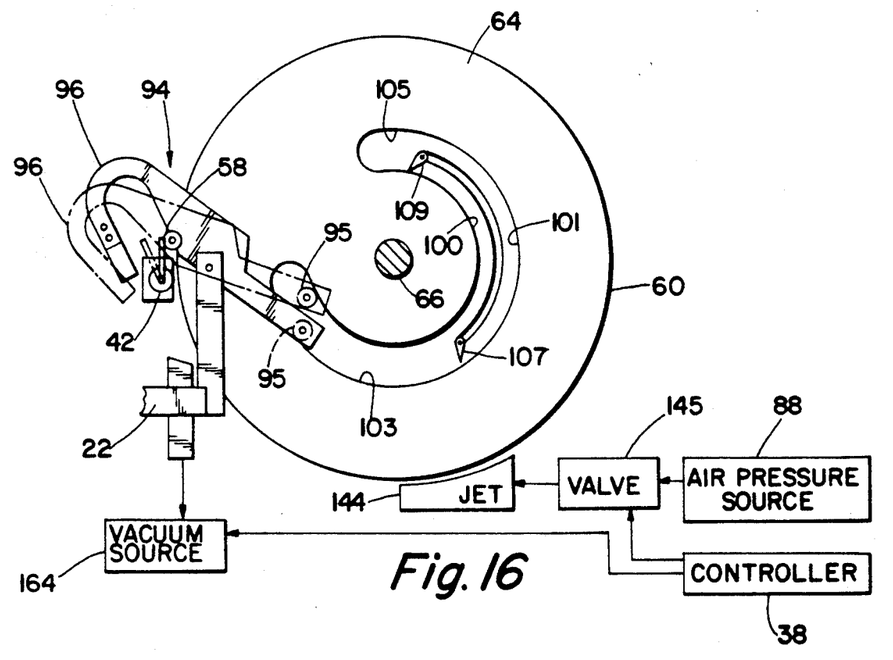
FIG. 16 is a side elevational view of one of the drums of the FIG. 1 apparatus and the associated linkage arrangement for moving the comb clamp between opened and closed positions.

Upon rotation of the drum 60 to the FIG. 12 end position, the rotation of the drum 60 is halted, and the cylinder 76 is actuated so that the hand plate 80 is retracted from the arcuate plate 70. As will be explained hereinafter, with the hand plate 80 retracted from the plate 70, the remainder of the fiber quantity 86 is freed and may be expelled from the drum 60 as waste. In the apparatus 20, an air jet 144 and a vacuum head 146 are suitably mounted beneath each drum 60 as depicted in FIG. 16 for blowing and drawing, respectively, the remainder of the fiber quantity 86 from each drum 60 as waste. In this connection, the jet 144 is connected to the air pressure source 88 by way of a valve 145, and the vacuum head 146 is connected to a vacuum source 164. The drum 60 is thereafter maintained in its FIG. 12 end position until completion of the testing operations upon the specimen. Near the completion of an operation cycle with the apparatus 20, the drum 60 is rotated by the cylinder assembly 108 from its FIG. 12 end position in a counter-clockwise direction as viewed in FIG. 12, and the comb clamp 42 is moved to its opened condition near the outset of the drum rotation. As the arcuate portion 90 of the drum 60 passes the comb 34 or 35 toward its FIG. 10 start position, the card wire 104 knocks the remains of the tested specimen fibers from the comb needles 48 so that the comb 34 or 35 is cleaned for a subsequent operation cycle. Upon return of the drum 60 to the FIG. 10 start position, the rotation of the drum 60 is halted and maintained in its FIG. 10 start position until a subsequent cycle of the apparatus 20 is initiated.

In order to move the comb clamp 42 between its opened and closed positions as described above and with reference to FIGS. 3, 4 and 16, the apparatus 20 includes a pair of linkage assemblies 94 supported by the frame 22 and cooperable with a camming groove 98 provided in the side plate 64 of each drum 60. In this connection, each linkage assembly 94 includes a link 96 pivotally supported by the frame 22 for moving the clamp 42 between its opened and closed positions as the link 96 is moved from its position as shown in solid lines in FIG. 16 to its position as shown in phantom in FIG. 16. Each linkage assembly 94 also includes a roller 95 rotatably attached to the link 96 and received by the camming groove 98. The camming groove 98 includes an inner groove track 100 which extends along the side plate 64 at a predetermined radius from the drum axle 66 and an outer groove track 101 which extends along the side plate 64 at a greater radius from the drum axle 66. The groove tracks 100, 101 communicate with one another through groove sections 103 and 105 located at the end of the groove tracks 100, 101. Spring-biased flippers 107, 109 are mounted at the ends of the tracks 100, 101 as shown in FIG. 16 to permit passage of the roller 95 out of each track 100 or 101 but prevent the return of the roller 95 into the track 100 or 101 from which it came.

As mentioned earlier, at the outset of a cycle with the apparatus 20, the comb clamp 42 is opened and the drum 60 is positioned in its first, or start, position as shown in FIGS. 3, 10 and 16. At that point, the roller 95 of the linkage arrangement 94 is positioned against the outer wall of the groove section 103 and the clamp 42 is opened with its lever 58 oriented vertically. Upon rotation of the drum 60 so that its arcuate plate 70 sweeps past the needles 48 of the comb 34 or 35, or clockwise as viewed in FIG. 16, the roller 95 is guided by the flipper 107 into the inner groove track 103 to move the link 96 to its FIG. 16 phantom-line position. As the link 96 is moved into its FIG. 16 phantom-line position, the link 96 pivots the clamp lever 54 from its vertical position to an angular position (illustrated in phantom in FIG. 16) at which the clamp 42 is closed. As the card wire-covered portion 90 of the drum 60 subsequently passes the comb 34 or 35, to card the fiber specimen held thereby, the clamp 42 is maintained in its closed position and the roller 95 moves past the flipper 109 and into the groove section 105 as shown in FIG. 4 where the drum 60 halts in its end position. Upon return of the drum 60 toward its start position, the roller 95 is guided into the outer groove track 101 by the flipper 109 so that the clamp 42 is opened. As the card wire 104 subsequently passes the comb needles 48, the specimen fibers 34 or 35 are knocked loose from the comb 34 or 35 and permitted to fall downwardly toward the vacuum head 146 (FIG. 16). When the drum 60 is thereafter halted in its start position, the roller 95 has moved past the flipper 107 and is positioned against the outer wall of the groove section 103 so as to be prepared for a subsequent cycle of the apparatus 20.

Figure 17:
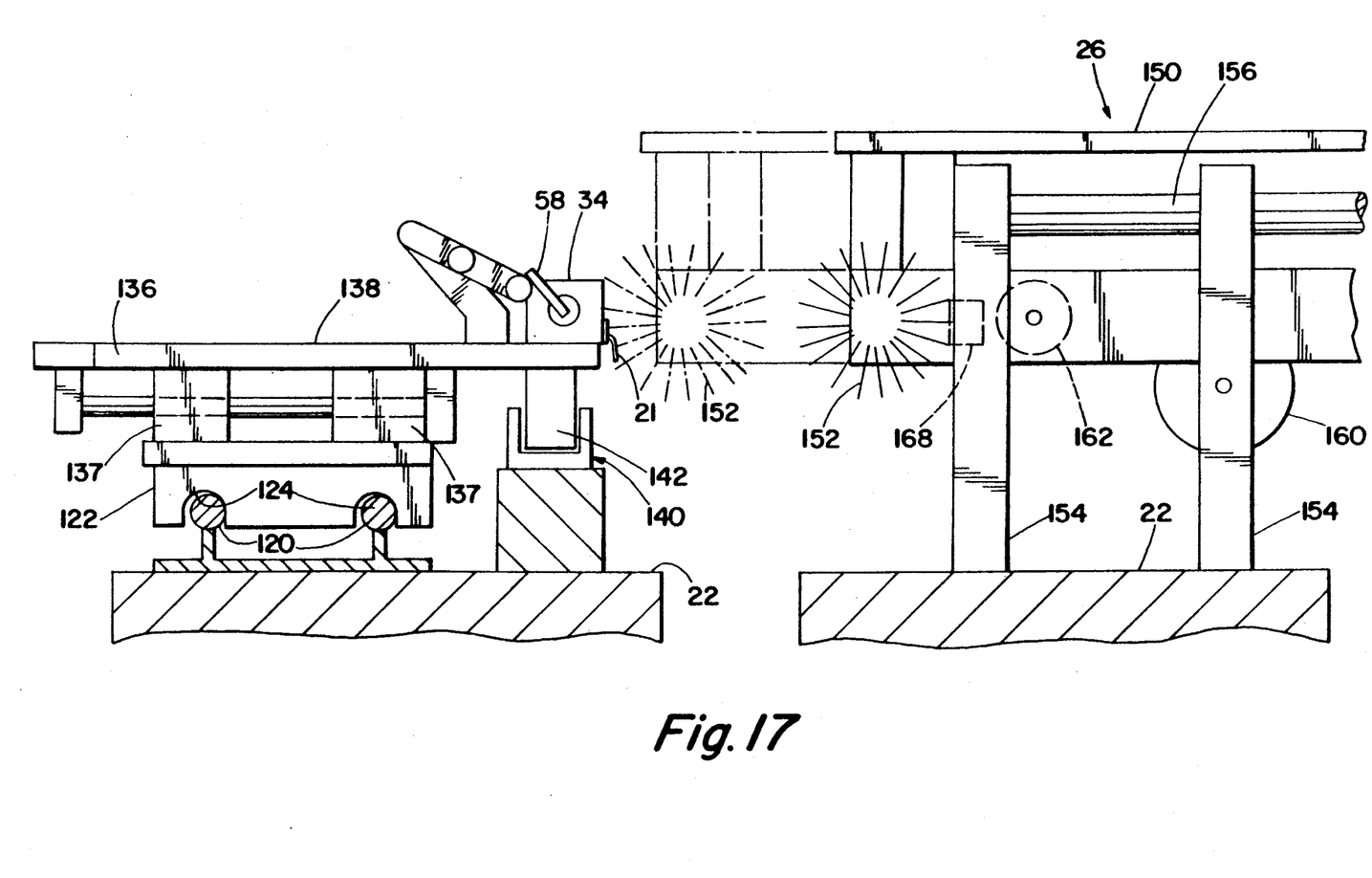
FIG. 17 is a schematic cross-sectional view of a comb of the FIG. 1 apparatus when positioned adjacent the brush means of the apparatus.

As will be explained hereinafter, once a specimen has been gathered by the combs 34 and 35, the combs 34, 35 are thereafter moved in sequence from the station in front of the holding means 24 and 25 as illustrated in FIG. 1 to a station in front of a brush means 26 where the specimens are brushed. As best shown in FIG. 17, the brush means 26 includes a carriage 150 supported by the frame 22 for movement in directions corresponding with Y-coordinate axis (illustrated in FIG. 1) and a rotary brush 152 mounted for rotation adjacent the front of the carriage 150 about a horizontal axis. For supporting the carriage 150, the frame 22 includes two sets of guide posts 154 positioned on opposite sides of the carriage 150, and the carriage 150 includes a set of guide rods 156 slidably received through aligned openings provided in the guide posts 154. A reversible stepping motor 160 is supported by the frame 22 adjacent the carriage 150 and is drivingly connected to the carriage 150 so that actuation of the stepping motor 160 in one rotational direction moves the carriage 150 relative to the frame 22 in one linear direction along the Y-coordinate axis and so that actuation of the stepping motor 160 in the other rotational direction moves the carriage 150 relative to the frame 22 in the opposite linear direction along the Y-coordinate axis. In the depicted apparatus 20, actuation of the stepping motor 160 in one rotational direction moves the carriage 150 from a home position as shown in solid lines in FIG. 17 to a working position as shown in phantom in FIG. 17 at which the specimen, indicated 21, held by the comb 34 or 35 can be brushed, and actuation of the stepping motor 160 in the opposite rotational direction returns the carriage 150 from its working position to its home position.

The brush means 26 also includes a reversible servomotor 162 supported by the carriage 150 and suitably connected to the brush 152 for rotating the brush 152 in either of its rotational directions about its rotation axis. As is apparent herein, the brush 152 brushes the specimen 21 when the brush 152 brushes the rotated in one direction (or the counter-clockwise direction as viewed in FIG. 17), and the brush 152 is cleaned when rotated in its opposite direction (or the clockwise direction as viewed in FIG. 17). The operation of the servomotor 162, as well as the operation of the stepping motor 160, is controlled by the controller 38.

Figure 22:
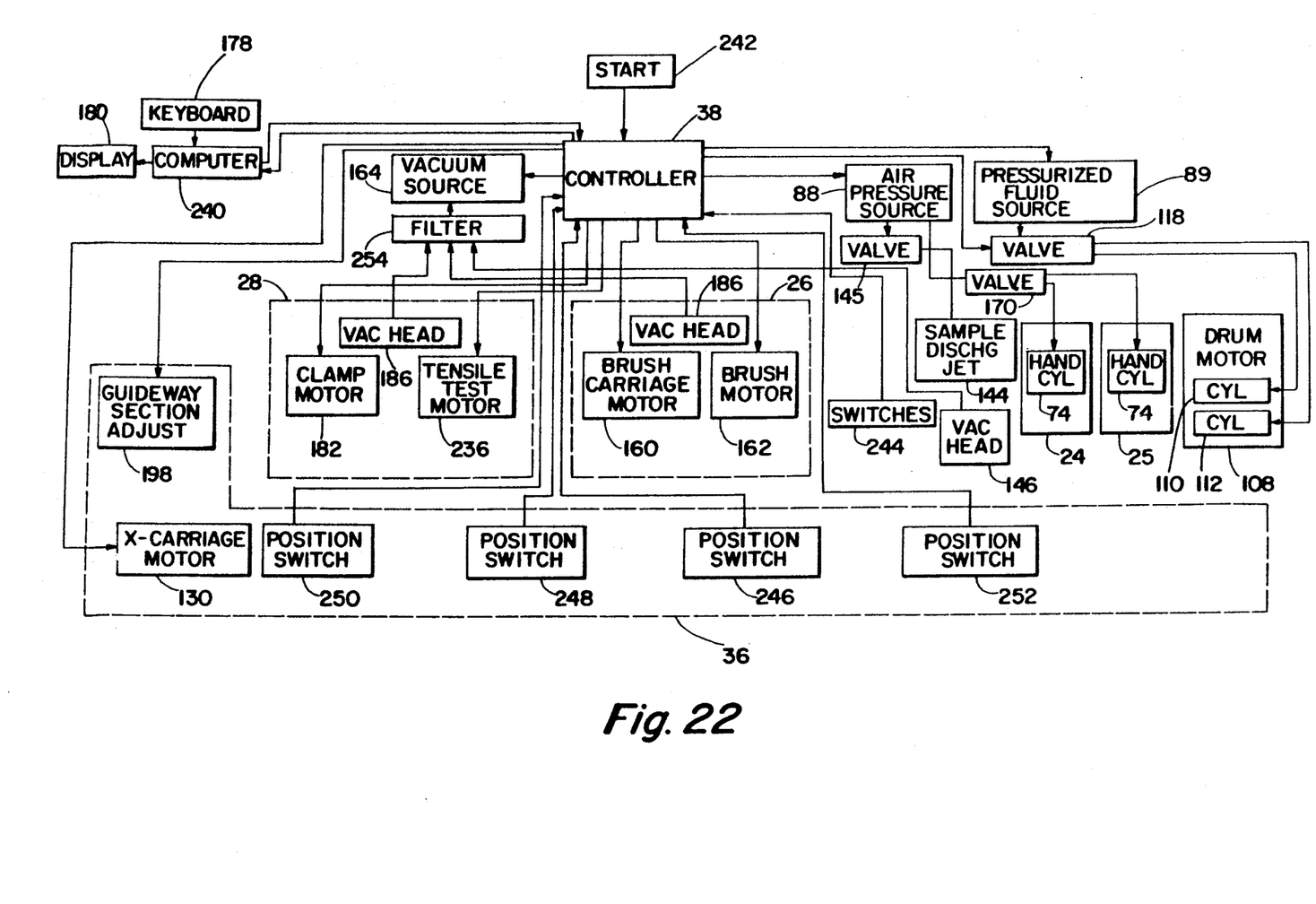
FIG. 22 is a view illustrating in block diagram form the control scheme of the FIG. 1 apparatus.

For cleaning the brush 152 as it is rotated in its brush-cleaning direction, a vacuum head 168 supported by the frame 22 and connected to the vacuum source 164 (FIG. 22). The head 168 is supported by the frame 22 in a stationary condition behind the brush 152 so that return of the carriage 150 to its home position brings the brush 152 to a position adjacent the head 168. By drawing a vacuum within the head 168 and simultaneously rotating the brush 152 in its brush-cleaning direction, beards or other fiber fragments which may have collected upon the surface of the brush 152 are pulled from the brush 152.

Figure 21:
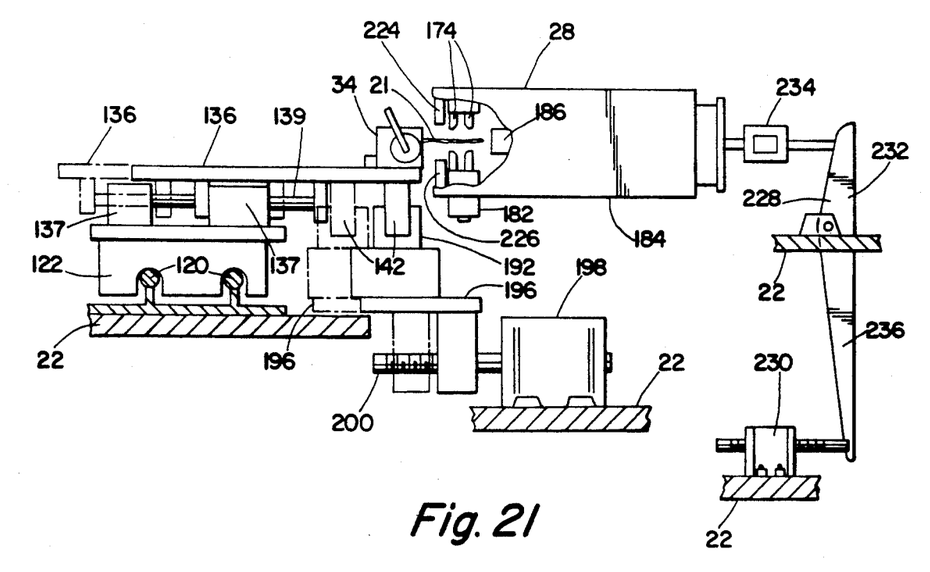
FIG. 21 is a schematic elevational view of a fragment of the FIG. 1 apparatus, shown partially cut-away, illustrating a comb of the apparatus when positioned in operative registry with the testing means.

Upon completion of a brushing operation at the brushing station, the specimen 21 is moved to a station in front of the testing means 28. As best shown in FIG. 21, the testing means 28 includes a pair of clamps 174, 176, each having an upper jaw and a lower jaw. During operation of the testing means 28, the fibers of the specimen 21 held within the comb 34 or 35 are clamped by the clamps 174, 176 at two locations along the length of the fibers so that the specimen fibers are tensioned between the clamps 174, 176. During a tensioning of the fiber specimen, characteristics of the specimen are measured, and information relating to the measured characteristics are sent to a computer 178 (FIG. 1) where the information may be stored in memory and/or viewed on a display screen 180.

With reference to FIG. 21, the testing means 28 includes a housing 184, and the clamps 174, 176 are positioned adjacent the front of the housing 184 for movement between opened and closed positions by means of a stepping motor 182 mounted beneath the housing 184. The stepping motor 182 is suitably geared to the clamps 174, 176 so that the rotational of the shaft of the motor 182 is translated to linear movement of the jaws of the clamps 174, 176 toward and away from one another. The testing means 28 also includes a vacuum head 186 mounted within the housing 184 for drawing the free ends of the specimen fibers held by the comb 34 or 35 between the open jaws of the clamps 174, 176 where the fibers are subsequently clamped and tested.

Although the testing means 28 may include any of several types of test equipment for performing tests upon the specimen, the depicted testing means 28 includes density-measuring means including a light source 226 mounted in the housing 184 generally below the specimen 21 and a light receiver 224 mounted in the housing 184 generally above the specimen 21 for measuring the amount of light transmitted through the specimen 21 from the source 224. The testing means 28 also includes tensile-measuring means including a lever 228 pivotally mounted within the frame 22 and operatively connected to one pair of the clamps 176 and a stepping motor 230 mounted within the frame 22 and connected to the lever 176. More specifically, the lever 228 has a response arm 232 which is connected to the pair of clamps 176 through a transducer 234 and an effort arm 236 which is connected to the shaft of the stepping motor 230 so that actuation of the stepping motor 236 tensions the fibers of the specimen 21 between the clamps 174, 176 until the fibers break. As the fibers are tensioned by the stepping motor 230, the force exerted upon the fibers is measured by the transducer 234 which, in turn, sends information relating to the measured force to the computer 178. At the end of a testing operation performed with the testing means 28, each set of clamps 174, 176 is moved to its open position so that the fibers of the specimen remaining in the comb 34 or 35 are freed from the clamps 174, 176. Fibers which are freed from the clamps 174, 174 and which do not remain attached to the comb 34 or 35 are drawn into the vacuum head 186 as waste.

For movement of the combs 34, 35 from the collection station adjacent the holding means 24, 25 and with reference again to FIG. 1, the moving means 36 includes a pair of guide rods 120 and an X-carriage 122 mounted upon the guide rods 120 for movement of the carriage 122 in the illustrated X-coordinate direction. The guide rods 120 are fixedly supported by the frame 22 so that the rods 122 are arranged in parallel relation with one another and span the length of the frame 22. The guide rods 120 are received by a pair of openings 124 provided in the body of the carriage 122 to facilitate movement of the carriage 122 along the rods 120.

In order to move the carriage 122 along the guide rods 120, the moving means 36 also includes a reversible motor 126 supported adjacent the frame end 30 and a cable/pulley arrangement 128 connected between the motor 126 and the carriage 122. More specifically, the cable/pulley arrangement 128 includes a first pulley 130 attached to the shaft of the motor 126 for rotation therewith and a second pulley 132 rotatably supported in the frame 22 adjacent the frame end 32. A cable 134 is wound about the first pulley 130, routed around the second pulley 134 and attached at its ends to opposite sides of the carriage 122 so that rotation of a first pulley 130 in one rotational direction moves the carriage 122 in one direction along the guide rods 120 and rotation of the first pulley 130 in the other rotational direction moves the carriage 122 in the other direction along the guide rods 120. Operation of the motor 126, and thus the movement of the X-carriage 122 along the guide rods 120, is controlled by the controller 38.

As best shown in FIG. 21, there is interposed between the X-carriage 122 and each comb 34 or 35 a Y-carriage 136 mounted for movement relative to the X-carriage 122 along the indicated Y-coordinate direction (FIG. 1). Each Y-carriage 136 includes a platen-like frame and a pair of guide rods 139 which are movably supported within pillow blocks 137 carried by the X-carriage 122 to permit, when desired, movement of the Y-carriage 136 traversely across the X-carriage 122. In particular, each Y-carriage 136 is movable relative to the X-carriage 122 between a home position, as illustrated in phantom in FIG. 21, and a test position, as illustrated in solid lines in FIG. 21. As will be apparent herein, the Y-carriage 136 is maintained in its home position relative to the Y-coordinate axis when the comb 34 or 35 carried by the Y-carriage 136 is positioned at the collection station adjacent the sample holding means 24 or 25 and at the brush station adjacent the brush means 26 and is moved to its test position relative to the Y-coordinate axis when positioned at the test station adjacent the testing means 28.

To ensure that each comb 34 or 35 remains in its desired position relative to the X-coordinate axis as the X-carriage 122 is moved along the guide rods 120, the apparatus 20 includes a channel-like guideway 140 supported by the frame 22 so as to extend longitudinally along the frame 22, and the Y-carriage 136 includes a downwardly-depending foot member 142 (FIGS. 3, 4 and 21) slidably received by the guideway 140.

Figure 18:
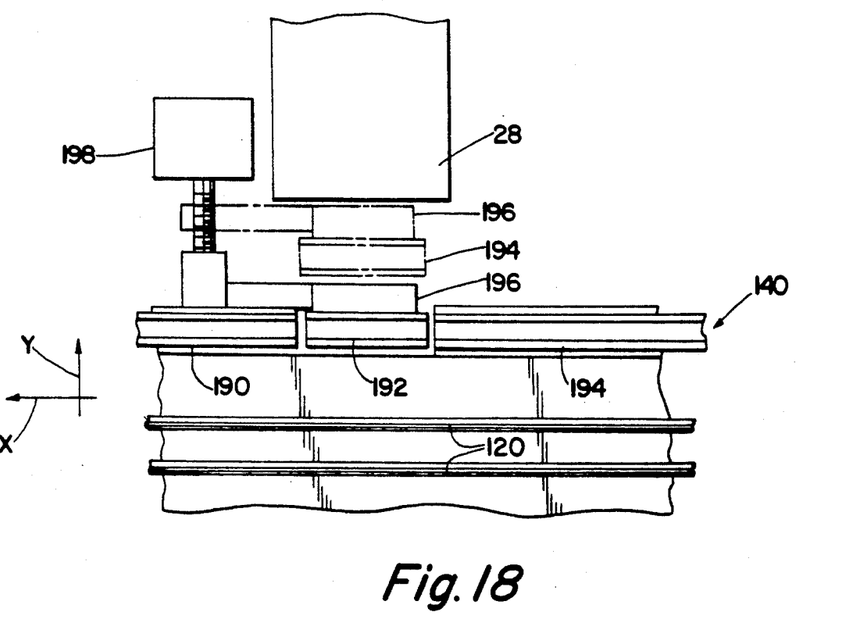
FIG. 18 is a plan view of a fragment of the FIG. 1 apparatus illustrating schematically the means used for moving a comb into registry with the testing means.
Figure 19:
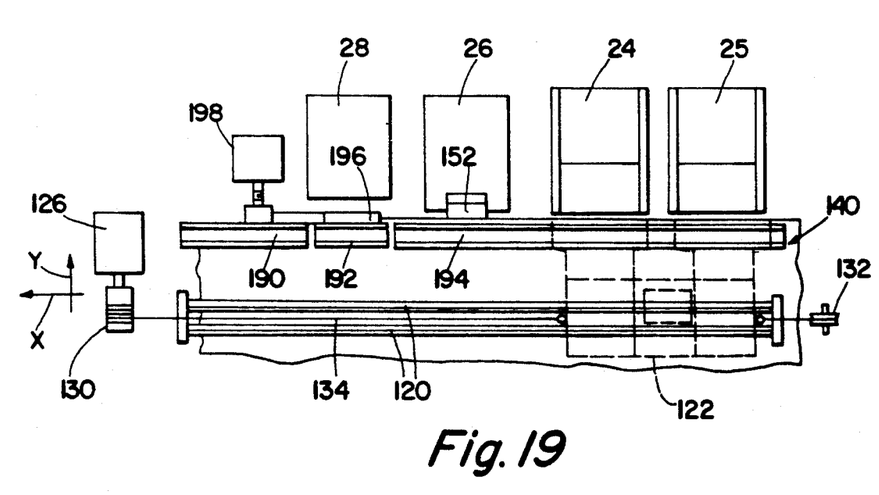
FIG. 19 is a plan view of a fragment of the FIG. 1 apparatus illustrating schematically the positional relationship of various components of the apparatus.

As best shown in FIG. 18 and 19, the guideway 140 includes three sections 190, 192 and 194 which are arranged in an end-to-end relationship along the length of the frame 22. Two sections 190 and 194 are fixed in a stationary condition within the frame 22 so as to align with one another, and the third section 192 is mounted for movement traversely of the frame 22. In particular, the apparatus 22 includes a movable support 196 upon which the guideway section 192 is fixedly secured for transverse movement of the guideway section 192 between a first position (illustrated in solid lines in FIG. 18) at which the guideway section 192 is aligned with the guideway sections 190 and 194 and a second position (illustrated in phantom in FIG. 17) at which its longitudinal axis is offset from that of the guideway sections 190, 194. As will be apparent herein, when the guideway section 192 is positioned in the aforementioned second, or offset, position, the fiber specimen held by one of the combs 34 or 35 is positioned in operative registry with the testing means 28. Associated with the movable support 196 is a stepping motor 198 mounted in the frame 22 having a threaded shaft 200 which is suitably geared to the movable support 196 for movement of the guideway section 192 between its first and second positions. Operation of the stepping motor 198, and thus the position of the guideway section 192 relative to the Y-coordinate axis, is controlled by the controller 38.

Figure 20:
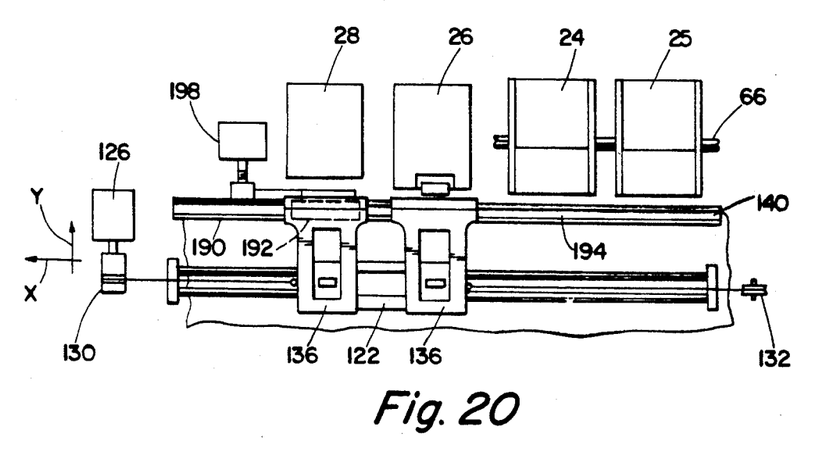
FIG. 20 is a view similar to that of FIG. 19 illustrating the X-carriage when positioned at one location along the frame.

With reference to FIGS. 19 and 20 and to position the comb 34 in registry with the testing means 28, the guideway section 192 is positioned in its first position at which it is aligned with the guideway sections 190 and 194 and the X-carriage 122 is moved along the length of the guide rods 120 until the Y-carriage 136 upon which the comb 34 is supported is positioned in front of the testing means 28 as illustrated in FIG. 20. With the Y-carriage 136 positioned as aforedescribed in front of the testing means 28, its foot member 142 is positioned within the guideway section 192 as illustrated in FIG. 21. At that point, the stepping motor 198 is energized to move the guideway section 192 from its first position to its second position so that the Y-carriage 136 is moved from its position illustrated in phantom in FIG. 20 to its position in front of the testing means 28 as illustrated in solid lines in FIG. 20. As the Y-carriage 196 is moved in this manner, the movement of its guide rods 139 is guided by the pillow blocks 137 of the X-carriage 122. With the Y-carriage 136 positioned in its FIG. 20 solid-line position, the specimen sample 21, is in a position to be tested by the testing means 28. Upon completion of the testing operations performed upon the specimen sample 21, the stepping motor 198 is reversed to return the guideway section 192 to its first position so that Y-carriage 136 can be guided along the other guideway sections 190, 194 as the X-carriage 122 is guided along the guide rods 120.

As mentioned earlier, the computer controller 38 controls the actuation of various components of the apparatus 20 and the sequencing of the stages of apparatus operation. In this connection and with reference to FIG. 22, the computer 178 and an associated keyboard 240 is connected to the controller 38 permitting an operator to input various programmable commands to the controller 38, and a start switch 242 is wired to the controller 38 enabling an operator to start each cycle of the apparatus 20 by pressing the switch 242.

Before a cycle of the apparatus 20 is initiated, the X-carriage 122 is positioned along the guide rods 120 as shown in FIG. 1 so that the comb 34 is positioned in registry with the sample holding means 24 and the comb 35 is positioned in registry with the sample holding means 25. Furthermore, the drums 60 of the sample holding means 24, 25 are positioned in their FIG. 10 start position with the hand plates 80 maintained in the retracted position. A quantity 86 of a fiber sample is then loaded within the hopper section 82 of each drum 60.

To initiate an operation cycle, the start switch 242 is pressed so that the controller 38 begins sending appropriate command signals to the various components to carry out the apparatus operations. In particular, and with reference again to FIG. 22, each air cylinder assembly 74 is actuated as the controller 38 sends appropriate command signals to the air source 88 and valve 170 so that each hand plate 80 moves to an extended position to press each quantity 86 of fiber against the corresponding drum plate 70. The cylinder 110 of the cylinder assembly 108 is then actuated through the valve 118 to rotate the drums 60 from the FIG. 10 start position toward the FIG. 12 end position. As the drum plates 70 move past the combs 34 and 35, specimen samples are collected by the comb needles 98. Upon movement of the plate 70 completely past the combs 34, 35, the linkage arrangements 94 mechanically close the comb clamps 42, and upon continued rotation of the drum plates 90 past the combs 34, 35, the collected specimens are carded by the card wire 104. The drums 60 are subsequently halted in the FIG. 12 end position, and each air cylinder assembly 74 is actuated by way of the valve 170 so that each hand plate 80 is retracted from its position adjacent the drum plate 70. The valves 145 are then actuated so that jets of air emitted from the jet 144 blow the fiber quantities 86 from the drums 60 and into the vacuum head 146. Fibers drawn toward the vacuum source 164 can be collected by a filter 254.

The vacuum source 164, which may be provided by a vacuum pump mounted within the frame 22, may be energized at the outset of an operation cycle so that it remains in operation throughout the cycle. Alternatively, magnetic switches 244 may be connected to one of the drums 60 so that the vacuum source 164 is energized only when the drum 60 moves through a predetermined range of angular positions. In the depicted apparatus 20, the switches 244 energize the vacuum source 164 so that a vacuum is drawn through the vacuum head 146 as long as the clamp 42 of each comb 34 or 35 is in its opened position.

The controller 38 then actuates the motor 126 so that the X-carriage 122 moved along the guide rods 120 to move the comb 34 toward the brushing station. A magnetic switch 246 is interposed between the X-carriage 122 and the frame 22 for de-actuating the motor 126 when the comb 34 is positioned in registry with the brush means 26. The controller 38 then sends appropriate command signals to the brush motors 160 and 162 so that the brush 152 is moved into engagement with the specimen held by the comb 34 and rotated in one direction so that the specimen is brushed. Upon completion of a brushing operation (which has been preprogrammed to last a predetermined period of time), the brush 152 is returned to its home position by the motor 160 and reversed in direction by the motor 162. A vacuum is drawn through the head 186 to clean the brush 152 as it is rotated in the reverse direction.

The motor 126 is subsequently re-actuated to move the X-carriage 122 by an incremental amount along the guide rods 120 so that the comb 34 is positioned in front of the testing means 28 and the comb 35 is positioned in front of the brush means 26. In this connection, a magnetic switch 248 is interposed between the X-carriage 122 and frame 22 at an appropriate location therealong for de-actuating the motor 126 when the comb 34 is positioned in front of the testing means 28 and the comb 35 is positioned in registry with the brush means 26. At that point, test operations are carried out by the testing means 28 upon the specimen held by the comb 34 at the same time that the specimen held by the comb 35 is brushed by the brush means 26. For performing test operations upon the specimen held by the comb 34, the controller 38 energizes the stepping motor 198 to move the comb 34 into registry with the testing means 28 and initiates the drawing of a vacuum through the head 186 so that the specimen is pulled between the open clamps 174, 176. The clamps 174, 176 are then closed and testing operations, including a measuring of the fiber density and a tensile test, are performed upon the specimen as test data is collected by the computer 178. The controller-controlled operations performed by the brush means 26 to brush the specimen held by the comb 35 are identical to those described earlier in connection with the brushing of the specimen held by the comb 34.

Upon completion of the testing operations by the testing means 28 upon the specimen held by the comb 34, the controller 38 opens the jaws of the clamps 174, 176 so that the specimen fibers held between the clamps 176 are drawn into the vacuum head 186, and the stepping motor 198 is again energized to return the comb 34 to its position upon the X-carriage 122 so that the guideway section 192 is aligned with the guideway sections 190 and 192. At that point, the X-carriage 122 is again advanced along the guide rods 120 until the comb 35 is positioned in front of the testing means 28. In this connection, a magnetic switch 250 is interposed between the Y-carriage 122 and the frame 22 at an appropriate location therealong for de-actuating the motor 126 when the comb 35 is positioned in front of the testing means 28. The operations of the testing means 28 which are subsequently initiated by the controller 38 to test the specimen held by the comb 35 are identical to those described earlier in connection with the testing of the specimen held by the comb 34.

Upon completion of the testing operations performed by the testing means 28 upon the specimen held by the comb 35, the controller 38 sends the appropriate command signals to the motor 126 so that the X-carriage 122 is moved in the reverse direction along the guide rods 120 and halted when the combs 34 and 35 are positioned at the collection station in front of the sample holding means 24, 25. In this connection, a magnetic switch 252 is interposed between the X-carriage 122 and the frame 22 at an appropriate location therealong so that the motor 126 is de-actuated when the comb 34 is positioned in front of the holding means 24 and the comb 35 is positioned in front of the holding means 25. The controller 38 then actuates the cylinder 112 of the cylinder assembly 108 to return the drums 60 toward the start position. Soon after the drums 60 begin their return rotation, the linkage arrangements 94 mechanically open the comb clamps 42 so that subsequent passage of the card wire 104 past the combs knocks the remaining fibers from the comb needles 48 where the fiber remains are drawn through the vacuum head 146. It follows that the card wire 104 is cleaned of debris as the card wire arrangement moves past the vacuum head 146. Upon return of the drums 60 to the start positions, the drum rotation is halted to thereby complete the operation cycle. It follows from the foregoing that the entire apparatus operation from the moment that the fiber quantity 86 is placed within each drum 60 to the moment that the drum 60 is returned to its start position is controlled automatically.

It will be understood that numerous modifications and substitutions can be had to the aforedescribed embodiment without departing from the spirit of the invention. For example, although the apparatus 20 has been shown and described as including two combs 34, 35 and two sample holding means 24, 25, an apparatus in accordance with the broader aspect of the present invention may include two combs and a single sample holding means, or a single comb and a single sample holding means. Accordingly, the aforedescribed embodiment is intended for the purpose of illustration and not as limitation.

We claim:

1. An apparatus for testing a specimen of fibers comprising:

sample holding means for holding a quantity of fibers from which a fiber specimen is to be gathered for testing;

testing means for performing at least one test upon the specimen of fibers when the specimen is positioned in registry with the testing means;

sampling means for gathering a specimen of fibers from the quantity of fibers held by the sample holding means and for holding the specimen during testing operations performed upon the specimen;

a movable carriage for supporting the sampling means; and carriage moving means associated with the carriage for moving the carriage so that the sampling means is positionable adjacent to the sample holding means for gathering a specimen of fibers from the quantity of fibers held by the holding means, and is positionable adjacent to the testing means so that the specimen is positioned in registry with the testing means for performing a test upon the fiber specimen.

2. The apparatus of claim 1 wherein the carriage is movable in a first direction between the sample holding means and the testing means and is movable in a second direction toward and away from the testing means; and the carriage moving means is operable to move the carriage and the specimen toward and away from the testing means.

3. The apparatus as defined in claim 1 wherein said sample holding means is supported for rotation, includes a sample-holding drum having a foraminous plate positioned along the periphery of the drum and is adapted to hold a quantity of fibers placed therein so that a portion of the fibers projects through the foraminous plate as the drum is rotated;

said sampling means includes a comb positioned to gather specimen fibers from the portion of the fibers which projects through the foraminous plate.

4. The apparatus as defined in claim 3 wherein said drum further includes an arrangement of card wire supported along the periphery of the drum and which arrangement trails the foraminous plate as the drum is rotated so that, after a specimen of fibers is gathered by the comb as the foraminous plate moves past the comb, the card wire arrangement moves past the gathered specimen so that the gathered specimen is carded by the card wire.

5. The apparatus as defined in claim 4 further comprising means for rotating the drum between two rotational positions so that as the drum is rotated between the two rotational positions, the foraminous plate and the card wire arrangement move in sequence past the comb.

6. The apparatus as defined in claim 5 wherein the sample-holding drum is a first drum and the comb is a first comb and the apparatus further comprises a second sample-holding drum rotatably supported by the frame adjacent the first drum and of construction like that of the first drum, and a second comb supported by the carriage adjacent the first comb and of construction like that of the first comb so that the first comb and second comb are positionable simultaneously adjacent a corresponding one of the first and second sample-holding drums for simultaneously gathering fiber specimens from the first and second drums by the first and second combs, and the controller is adapted to move each of the first and second combs in sequence from the positions adjacent the sample-holding drums to the second location at which the fiber specimens are tested.

7. The apparatus as defined in claim 5 wherein the comb includes a comb body secured in a stationary condition upon the carriage and a comb clamp movably attached to the comb body for movement between opened and closed positions, the comb body including a plurality of fiber-gathering needles which cooperate with the comb clamp so that when the comb clamp is in its opened position, the comb needles are exposed for gathering a fiber specimen as the foraminous plate moves past the comb and so that, when the clamp is in its closed position, the fiber specimen gathered by the comb needles are firmly retained by the comb, and the apparatus further includes means for automatically moving the clamp from its opened position to its closed position after the foraminous plate has moved past the comb and before the card wire arrangement moves past the comb.

8. The apparatus as defined in claim 7 wherein the clamp moving means include mechanical means associated with the drum and carriage for moving the clamp from its opened position to its closed position as aforesaid.

9. The apparatus as defined in claim 1 further comprising a brush and a brush carriage positioned between the sample holding means and the testing means, the carriage moving means adapted to move the specimen into registry with said brush, the brush being rotatably supported upon the brush carriage and the brush carriage being movably supported for movement of the brush into and out of engagement with the specimen.

10. The apparatus of claim 1 wherein said sampling means comprises at least two samplers, said carriage moving means being operable to move each sampler into registry with the sample holding means and the testing means.

11. The apparatus of claim 1 further comprising means for automatically ejecting fibers from said sample holding means after the sampling means has gathered a specimen of fibers from said sample holding means.

12. A fiber testing apparatus comprising:

an elongated frame;

sample holding means mounted within the frame at a first location therealong for movement relative to the frame and adapted to hold a quantity of fibers out of which a fiber specimen is to be gathered for testing;

means for moving the sample holding means relative to the frame between two positions of movement, the sample holding means having a foraminous surface which moves along a predetermined path as the sample holding means is moved relative to the frame between the two positions of movement and including a hopper section for holding the quantity of fibers so that a portion of the quantity of fibers protrude out of the hopper section through the foraminous surface;

a comb positionable at a first station adjacent the sample holding means for gathering a fiber specimen from the quantity of fibers held thereby so that as the foraminous surface is moved along the predetermined path, a fiber specimen sample is gathered by the comb;

card means associated with the sample holding means for carding the gathered fiber specimen as the sample holding means is moved between its two positions of movement;

a brush rotatably supported by the frame at a second location therealong for brushing the fiber specimen sample when the comb is moved relative to the frame to a second station adjacent the brush and the brush is rotated in engagement with the gathered fiber specimen;

means connected to the brush for rotating the brush;

testing means supported by the frame at a third location therealong for testing the fiber specimen when the comb is moved relative to the frame to a third station adjacent the testing means; and a carriage movably mounted upon the frame for movement therealong and for supporting the comb along the frame; and means associated with the carriage for moving the carriage along the frame so that the comb is positionable at the first location adjacent the sample holding means for gathering a fiber specimen from the quantity of fibers held by the holding means as the holding means is moved relative to the frame, is positionable at the second station adjacent the brush means for brushing of the fiber specimen by the brush as the brush is rotated, and is positionable at the third station adjacent the testing means so that the fiber specimen is positioned in registry with the testing means for performing a test upon the fiber specimen.

13. An apparatus for testing a specimen of fibers comprising;

sample holding means for holding a specimen of fibers;

a sampler for engaging the specimen of fibers, removing a sample of fibers from the specimen and holding the sample;

drive means for moving the sample holding means past the sampler while the sample is stationary so that the sampler removes a sample of fibers from the specimen in the holding means;

means for testing at least one characteristic of the sample; and means for automatically moving the sampler between a first position at which the sampler is in a position for engaging and removing a sample of fibers from the specimen as the sample holding means is moved past the sampler and a second position means at which the sample of fibers held by the sampler is in a position to be tested by the testing means.

14. The apparatus of claim 13 further comprising:
a clamp for selectively clamping the sample in the sampler; and
actuation means for actuating the clamp to clamp the sample after the sample holding means moves past the sampler.

15. The apparatus of claim 13 further comprising:

a clamp for selectively clamping and unclamping the sample in the sampler; and
actuation means for actuating the clamp to unclamp the sample after the completion of a test performed upon the sample.

16. The apparatus of claim 13 wherein:
the sample holding means comprises:
a drum having a cylindrical face and a center axis;
means for supporting the drum for rotation about the center axis;
a foraminous plate forming part of the cylindrical face; and
a presser mounted inside the drum for pressing the specimen of fibers against the inside surface of the foraminous plate so that portions of the specimen protrude through the foraminous face;
said drum means is adapted to rotate said drum; and
said sampler is positioned to engage the fibers protruding through the foraminous plate as the plate moves past the sampler.

17. An apparatus for testing a specimen of fibers comprising:
sample holding means for holding a quantity of fibers from which a fiber specimen is to be gathered for testing;
testing means for performing at least one test upon the specimen of fibers when the specimen is positioned in registry with the testing means;
sampling means for gathering a specimen of fibers from the quantity of fibers held by the sample holding means and for holding the specimen during testing operations performed upon the specimen; and
transport means associated with the sampling holding means for automatically moving the sampling means from a position adjacent the sample holding means at which a specimen of fibers is gathered from the quantity of fibers to a position adjacent the testing means at which the fiber specimen held by the sampling means is positioned in registry with the testing means for performing a test upon the specimen.

18. An apparatus for testing a specimen of fibers comprising:
sample holding means for holding a specimen of fibers;
a sampler for engaging the specimen of fibers, removing a sample of fibers from the specimen and holding the sample;
drive means for moving the sample holding means and sampler relative to one another so that the sampler removes a sample of fibers from the specimen held by the sample holding means; and
means for testing at least one characteristic of the sample; and
the sample holding means includes a drum within which the specimen of fibers is positionable and includes a curved face and an axis, means for supporting the drum for movement relative to the sampler, a foraminous plate forming part of the curved face of the drum, and presser means mounted inside the drum for pressing the specimen of fibers against the inside surface of the foraminous plate so that portions of the specimen protrude through the foraminous plate and so that as the sample holding means and sampler are moved relative to one another, the sampler engages the fibers protruding through the foraminous plate for removal of a sample of fibers therefrom.

19. The apparatus as defined in claim 18 further comprising:

said presser means being operable to retract and release the specimen of fibers from the pressed condition against the foraminous plate; and air jet means supported adjacent the drum for directing an air jet into the drum to blow the remainder of the specimen of fibers from the drum following the gathering of a sample of fibers by the sampling means and the release of the fibers by the presser means.

20. The apparatus as defined in claim 18 wherein said presser means further comprises a flexible hand member for engaging the specimen of fibers.

* * * * *